United States Patent
Kanda et al.

(10) Patent No.: US 10,870,814 B2
(45) Date of Patent: Dec. 22, 2020

(54) METHODS FOR FRACTIONATING LIPIDS

(71) Applicant: NIPPON SUISAN KAISHA, LTD., Tokyo (JP)

(72) Inventors: Hideki Kanda, Aichi (JP); Motonobu Goto, Aichi (JP); Yuji Okita, Tokyo (JP); Eiji Ohashi, Tokyo (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 95 days.

(21) Appl. No.: 15/301,087

(22) PCT Filed: Mar. 30, 2015

(86) PCT No.: PCT/JP2015/059895
§ 371 (c)(1),
(2) Date: Sep. 30, 2016

(87) PCT Pub. No.: WO2015/152144
PCT Pub. Date: Oct. 8, 2015

(65) Prior Publication Data
US 2017/0022448 A1    Jan. 26, 2017

(30) Foreign Application Priority Data
Mar. 31, 2014  (JP) ................... 2014-071748

(51) Int. Cl.
C11B 1/10   (2006.01)
C11B 7/00   (2006.01)
C12P 7/64   (2006.01)

(52) U.S. Cl.
CPC ............... *C11B 7/005* (2013.01); *C11B 1/10* (2013.01); *C11B 1/104* (2013.01); *C11B 7/0025* (2013.01); *C12P 7/6409* (2013.01); *C12P 7/6472* (2013.01)

(58) Field of Classification Search
None
See application file for complete search history.

(56) References Cited

U.S. PATENT DOCUMENTS

| | | | |
|---|---|---|---|
| 2004/0161831 A1 | 8/2004 | Komazawa et al. | |
| 2008/0009045 A1 | 1/2008 | Komazawa et al. | |
| 2008/0146851 A1 | 6/2008 | Schonemann et al. | |
| 2012/0282662 A1* | 11/2012 | Kale | C11B 1/10 435/134 |

FOREIGN PATENT DOCUMENTS

| | | |
|---|---|---|
| CN | 101892160 A | 11/2010 |
| JP | 2005102680 A | 4/2005 |
| JP | 2007143479 A | 6/2007 |
| JP | 201094111 A | 4/2010 |
| JP | 2010240609 A | 10/2010 |
| JP | 201131170 A | 2/2011 |
| JP | 4934272 B2 | 2/2012 |

OTHER PUBLICATIONS

Kaya ("Thraustochytrid *Aurantiochytrium* sp. 18W-13a Accumulates High Amounts of Squalene" Bioscience, Biotechnology and Biochemistry, 75 (11), 2246-2248 2011) (Year: 2011).*

Holldorff ("Binary Vapor-Liquid-Liquid Equilibrium of Dimethyl Ether—Water and Mutual Solubilities of Methyl Chloride and Water", Fluid Phase Equilibria 44 (1988), 195-209). (Year: 1988).*

Shen ("Identification of Characteristic Fatty Acids to Quantify Triacylglycerols in Microalgae", Frontiers in Plant Sciences, 2016, 7:162) (Year: 2006).*

H. Kanda et al., "Lipids extracted from several species of natural blue-green microalgae by dimethyl ether: Extraction yield and properties," SciVerse Science Direct; Fuel 95, 2012, pp. 88-92.

Hideki Kanda "New Oil Extraction Assists Microalgae to Fuel Processes in Reaching a Positive Energy Balance by Exergy Recuperation" Journal of the Japan Institute of Energy, 2012, vol. 91, No. 9, p. 1172-1176, with English translation.

Hideki Kanda "Technical Report Technology for Highly Efficient Extraction of "Green Crude Oil" From Blue-Green Algae" Clean Energy, 2010, vol. 19, No. 10, p. 59-63, with English translation.

(Continued)

*Primary Examiner* — Robert J Yamasaki
*Assistant Examiner* — Charles Zoltan Constantine
(74) *Attorney, Agent, or Firm* — Cantor Colburn LLP

(57) ABSTRACT

[Problem] Provision of a method for fractionating lipids using liquefied dimethyl ether as a solvent.

[Means for Solving] To provide a method for fractionating a lipid using liquefied dimethyl ether as a solvent. [Solution] A method for fractionating a lipid, which comprises subjecting a microbial biomass to extraction using liquefied dimethyl ether as a solvent and then fractionating the lipid utilizing separation selectivity for the lipid. A method for producing a lipid, which comprises subjecting a microbial biomass to extraction using liquefied dimethyl ether as a solvent, then fractionating a portion of the lipid utilizing separation selectivity for the lipid to modify the fatty acid composition of the remainder of the lipid which remains in the microbial biomass, and then extracting the lipid having a modified fatty acid composition.

18 Claims, 1 Drawing Sheet

(56) References Cited

OTHER PUBLICATIONS

Hideki Kanda et al. "Wet extraction of hydrocarbons from Botryococcus braunii by dimethyl ether as compared with dry extraction by hexane" Fuel 105 (2013) 535-539.
Hideki Kanda, "Method of Extracting Oil and Water From Wet Biomass by Converting Unharnessed Waste Heat to Separation Energy With DME" Chemical Engineering of Japan, 2013, vol. 77, No. 9, p. 620-623, with English translation.
International Search Report corresponding to Application No. PCT/JP2015/059895; dated Jun. 2, 2015, with English translation.
James Wynn et al. "Production of Single Cell Oils by Dinoflagellates in Single Cell Oils" AOCS Press, Champaign, Illinois, 2005, pp. 86-98.
Shokuhin Kogyo "Food Industry" 2007, vol. 50, No. 6, p. 56-62, with partial English translation.

* cited by examiner

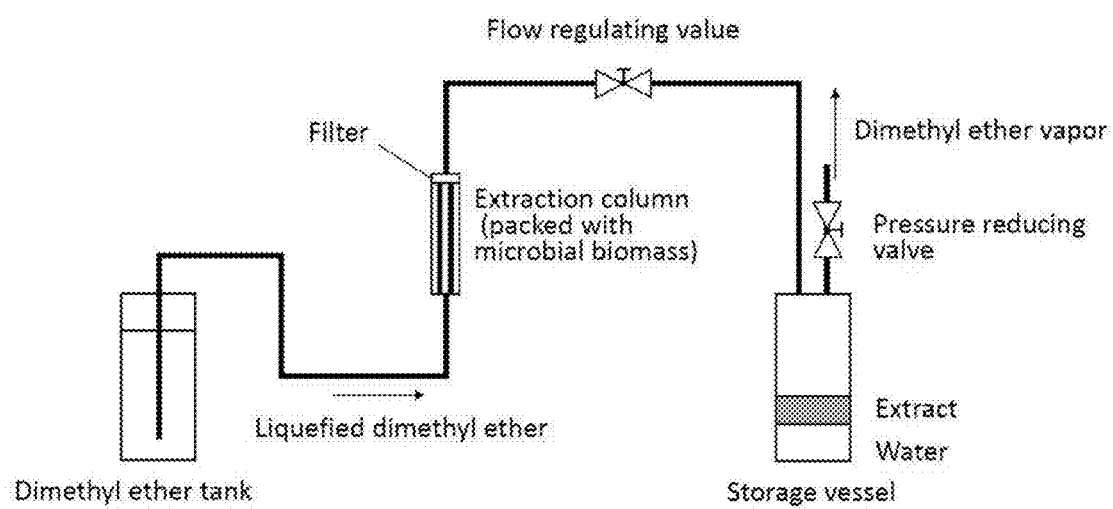

METHODS FOR FRACTIONATING LIPIDS

This is the U.S. national stage of application No. PCT/JP2015/059895, filed on Mar. 30, 2015. Priority under 35 U.S.C. § 119(a) and 35 U.S.C. § 365(b) is claimed from Japanese Application No. 2014-071748, filed Mar. 31, 2014, the disclosure of which is also incorporated herein by reference.

TECHNICAL FIELD

The present invention relates to methods for fractionating lipids from microbial biomass, more particularly, to methods for fractionating lipids by making use of the selectivity of liquefied dimethyl ether for separation in lipid extraction.

BACKGROUND ART

As methods for extracting lipids from microbial biomass, solvent extraction using organic solvents such as hexane, extraction with supercritical carbon dioxide, and various other extraction techniques are conventionally known and have been utilized extensively. Microorganisms such as the dinoflagellate *Crypthecodinium cohnii*, the labyrinthelea *Aurantiochytrium limacinum* (also known as *Schizochytrium limacinum*) and the filamentous fungus *Mortierella alpina* are known to produce lipids that contain useful, highly unsaturated fatty acids such as docosahexaenoic acid and arachidonic acid. The highly unsaturated fatty acid containing lipids that are produced by those microorganisms are commercially produced by more than one company and extensively used as additives to infant formulas or as ingredients in foods. To produce these lipids, a method is known that performs extraction from cells by solvent extraction which uses organic solvents such as hexane (Non-Patent Document 1). The green alga *Haematococcus pluvialis* which is in a class of microalgae is known to accumulate astaxanthin at high concentration in dormant spores (cyst cells) under controlled culture conditions and astaxanthin production using this alga has also been commercialized by more than one company, and to extract astaxanthin from cells, solvent extraction is performed using organic solvents such as acetone (Patent Document 1) or extraction is performed with supercritical carbon dioxide (Non-Patent Document 2).

In addition to these conventional extraction methods, there is another method that is drawing attention in recent years and it uses liquefied dimethyl ether (hereinafter sometimes abbreviated as DME) as a solvent. The advantage of this method is that it has no need to dry biomass, disrupt cells and remove the organic solvent used for extraction (Patent Documents 2 and 3). This extraction method which uses liquefied dimethyl ether does not involve any steps that require heating, such as drying of the feed and removal of the solvent from the extract, so if it is used to extract lipids from the feed, say, microbial biomass, lipid oxidation is minimized to allow for the production of high-quality lipids. As a further advantage, the energy required for drying, disrupting and solvent removal is saved to thereby realize lipid production at a lower energy cost.

CITATION LIST

Patent Literature

Patent Document 1: Japanese Patent No. 4934272
Patent Document 2: JP 2010-240609 A
Patent Document 3: JP 2011-031170 A

Non-Patent Literature

Non-Patent Document 1: James Wynn, Paul Behrens, Anand Sundararajan, Joe Hansen, and Kirk Apt, Production of Single Cell Oils by Dinoflagellates, in Single Cell Oils, Zvi Cohen, and Colin Ratledge, eds., AOCS Press, Champaign, Ill., 2005, pp. 86-98.

Non-Patent Document 2: Toshihiro Okamura, Shokuhin Kogyo ("Food Industry" in English), Vol. 50, No. 6, p. 56-62, Kohrin (2007)

SUMMARY OF INVENTION

Technical Problem

The above-described extraction method of Patent Document 2 which uses liquefied dimethyl ether as a solvent is a technique that extracts all oil contents that can be extracted from the material of interest.

The present inventors thought that it might be possible to apply this liquefied DME-based extraction method in fractionating lipids and got the basic idea of the present invention. An object, therefore, of the present invention is to provide a method for fractionating lipids using liquefied DME as a solvent.

Solution to Problem

The present inventors performed extraction on microbial biomass using liquefied dimethyl ether as a solvent—this compound has not so far been known to have separation selectivity for lipids—and fractionated the extract over time; as a result, the inventors found that the compositions of fatty acids in the fractions varied depending on the fractionation time and this has led to the accomplishment of the present invention. Briefly, an object of the present invention is to provide a new method for fractionating lipids from microbial biomass.

In essence, the present invention relates to the methods described below in (1) to (7).

(1) A method for fractionating lipids comprising subjecting microbial biomass to extraction using liquefied dimethyl ether as a solvent by making use of the separation selectivity of the liquefied dimethyl ether for lipids.

(2) A method for altering composition of fatty acids in lipids in microbial biomass comprising subjecting microbial biomass to extraction using liquefied dimethyl ether as a solvent and removing part of lipids by making use of the separation selectivity of the liquefied dimethyl ether for lipids to thereby alter the composition of fatty acids in the remaining lipids in the microbial biomass.

(3) A method for producing lipids comprising extracting lipids with an altered composition of fatty acids from the microbial biomass that has been altered in the composition of fatty acids by the method of (2).

(4) The method as recited in any one of (1) to (3), wherein the microbial biomass is biomass obtained by culturing a microorganism in the class Labyrinthulea.

(5) The method as recited in (4) wherein the microorganism in the class Labyrinthulea belongs to the genus *Aurantiochytrium*.

(6) The method as recited in any one of (1) to (3), wherein the microbial biomass is biomass obtained by culturing a microorganism in the class of green algae.

(7) The method as recited in (6) wherein the microorganism in the class of green algae belongs to the genus *Haematococcus*.

Advantageous Effects of Invention

According to the present invention, there can be provided a new method for fractionating lipids from microbial biomass using liquefied DME as a solvent. For example, by simply performing fractionation using liquefied DME, separation can be realized between lipids that are rich in saturated fatty acids and lipids that are rich in highly unsaturated fatty acids.

BRIEF DESCRIPTION OF DRAWINGS

FIG. 1 is a schematic diagram showing one mode of an apparatus to be used in the present invention.

DESCRIPTION OF EMBODIMENTS

In the present invention, intracellular lipids of microbial biomass are recovered through fractionation by making use of the differential selectivity of liquefied DME for lipids.

The liquefied DME (IUPAC name: methoxymethane) to be used in the present invention has a boiling point of −23.6° C., so it assumes the gaseous state at normal temperature. The gas is brought back to the liquid state for use as a solvent in the present invention. To liquefy DME, adjustments can be appropriately made within the ranges of from about 0.25 to about 1.14 MPa for pressure and from about 0 to about 50° C. for temperature.

The term "microorganism" as used in the present invention refers to those microorganisms which produce lipids in their cells. Examples are microorganisms that belong to the genera *Crypthecodinium, Thraustochytrium, Schizochytrium, Ulkenia Japonochytrium, Haliphthoros, Mortierella, Penicillium, Aspergillus, Rhodotorula*, and *Fusarium*. Specific examples are microorganisms such as the dinoflagellate *Crypthecodinium cohnii*, the labyrinthelea *Aurantiochytrium limacinum* (also known as *Schizochytrium limacinum*) and the filamentous fungus *Mortierella alpina*, as well as the green alga *Haematococcus pluvialis*.

The term "lipids" as used in the present invention refers to those lipids which are produced by microorganisms and typical examples include triglycerides, diglycerides, monoglycerides, phospholipids, free fatty acids, sterols, hydrocarbons, etc. If desired, components like pigments contained in microorganism-produced lipids, such as astaxanthin and other carotenoids, can also be fractionated together with the lipids.

The composition of fatty acids bound to lipids varies with the microorganism but, typically, fatty acids having 12-24 carbon atoms and 0-6 double bonds are contained in varying proportions. Fatty acids that have physiological activities and are held useful are highly unsaturated fatty acids, which are fatty acids having at least 18 carbon atoms and at least 3 double bonds, more preferably fatty acids having at least 20 carbon atoms and at least 3 double bonds. Specific examples include α-linolenic acid (18:3, n-3), γ-linolenic acid (18:3, n-6), arachidonic acid (20:4, n-6), di-homo-γ-linolenic acid (20:3, n-6), eicosapentaenoic acid (20:5, n-3), docosapentaenoic acid (22:5, n-6), docosahexaenoic acid (22:6, n-3), etc.

Lipids in microbial cells have these fatty acids bound thereto as constituent fatty acids in triglycerides, phospholipids, or the like.

The simplest way to make use of the separation selectivity of liquefied DME for lipids comprises packing a column with microbial cells, causing liquefied DME to flow through the column at a specified rate, and fractionating the effluent. As will be shown in Examples later, liquefied DME offers selectivity in the process of eluting lipids from the microbial cells.

Liquefied DME allows for early elution of lipids that contain saturated fatty acids whereas the elution of lipids that contain highly unsaturated fatty acids is delayed. This difference in elution rate is effectively used to increase the concentration of highly unsaturated fatty acids contained in the lipids. The same result can be obtained without using the column but by a batch process repeating runs of extraction with a small amount of liquefied DME. Any other type of apparatus may be employed if it exhibits the same effect.

In the conventional case of solvent extraction from microbial cells, high efficiency is realized in extraction by using hexane, for example, but since hexane has only low separation selectivity for lipids, the composition of fatty acids in the extracted neutral lipids is basically the same as the composition of fatty acids in the neutral lipids in the microbial biomass. If the highly unsaturated fatty acids in the extracted lipids need to be concentrated, a separate purification step is performed after the extraction. Known methods of purification that can alter the composition of fatty acids include urea adduct separation methods, winterization, precision distillation, and lipase-based concentration, and these methods share the principle of altering the composition of fatty acids on the basis of differences in their properties such as molecular weight or the number of unsaturated bonds.

According to the method of the present invention, highly unsaturated fatty acids can already be concentrated to a certain extent at the stage of extraction from the microbial biomass. If desired, separation by the method of the present invention may be followed by purification by the above-described conventional methods.

The above-described separation selectivity of liquefied DME can be utilized to selectively remove saturated and other unwanted fatty acids by extraction from microbial cells and, thereafter, all of the remaining lipids are extracted with hexane or other organic solvents.

By means of fractionation with liquefied DME, pigments such as astaxanthin that are contained in lipids are concentrated together with the lipids that are rich in those pigments and may be immediately used as concentrated pigments; alternatively, they may be further purified by applying methods for astaxanthin purification such as extraction with supercritical carbon dioxide.

On the following pages, working examples of the present invention will be described but it should be understood that the present invention is by no means limited to these examples.

The structural setup of the extraction apparatus used in the working examples is shown in FIG. 1. An extraction column to be packed with a microorganism (HPG-10-5; product of TAIATSU TECHNO; 180 mm×26 mm (i.d.)) was connected at the outlet to a storage vessel (HPG-96-3; product of TAIATSU TECHNO; capacity 96 cm$^3$) by means of a stainless steel tube. The extraction column and the storage vessel were each a pressure-resistant vessel made of glass and a polycarbonate resin. Liquefied dimethyl ether as supplied from a dimethyl ether tank was flowed to the extraction column packed with microbial cells and the extract from the extraction column was recovered into the storage vessel. After extraction was performed for a prescribed time, the pressure reducing valve on the storage vessel was opened, whereupon dimethyl ether was evaporated away to leave a mixture of the extract and water, which was then recovered from the storage vessel.

Example 1

Extraction of Lipids from Labyrinthulea

An inoculum of *Aurantiochytrium limacinum*, a microorganism belonging to the class Labyrinthulea, was cultured in a GY medium (30 g glucose and 10 g yeast extract were dissolved in 1 L of 50% artificial seawater and adjusted to pH 7.0). Specifically, 30 mL of the GY medium was poured into a 50 mL Erlenmeyer flask and cultured for 3 days at 28° C. with shaking at 100 rpm. Cells were collected from the culture broth by centrifugation, washed with distilled water to remove the medium components, and cells were collected by further centrifugation. The collected cells were lyophilized to make microbial biomass. The thus obtained microbial biomass was stored in a freezer at −20° C. until it was subjected to extraction.

To 0.33 g of the lyophilized microbial biomass, 1.263 g of distilled water was added and the mixture was stirred well to make a sample, which was subjected to extraction, with fractionation being performed, using the apparatus of FIG. 1. In the process, the flow rate of liquefied dimethyl ether was set at 5 mL/min. The temperature of the extraction column was set at 20° C. and the pressure at 0.51 MPa. The microbial biomass was rendered hydrous through addition of distilled water and this was in order to reproduce the state of microbial cells that were close to those which had been collected from the culture broth. In the process, no operation was conducted for disrupting cells.

The extract was fractionated at the time intervals indicated in Table 1. The respective fractions obtained by flowing liquefied dimethyl ether were reverted to normal temperature and pressure, whereupon the dimethyl ether was evaporated away from the extract in each fraction. Subsequently, a dried gas (which was dimethyl ether in Example 1) was brought into adequate contact with the extract, so that moisture was removed from the extract in each fraction to give oils in the amounts indicated in Table 1.

TABLE 1

|  | Fraction No. | | | | | | |
| --- | --- | --- | --- | --- | --- | --- | --- |
|  | 1 | 2 | 3 | 4 | 5 | 6 | Total |
| Time (min) | 2 | 7 | 17 | 33 | 49 | 65 |  |
| Oil (mg) | 12 | 32 | 33 | 10 | 9 | 1 | 97 |

Note:
The weights of oils with fraction Nos. 1 to 6 are found values and the total weight is a calculated value.

From the thus obtained oils, fatty acid methyl esters were prepared and subjected to gas chromatographic analysis of the composition of fatty acids. For the analysis, a gas chromatograph (Agilent Technologies 7890A GC System) and a column (J&W DB-WAX; 0.25 mm i.d.× 30 m long, with film thickness of 0.25 μm) were used under such conditions that the column temperature (gradient) was 140° C.→240° C. (4° C./min), with holding at 240° C. for 10 minutes, and that He was used as a carrier gas (1.05 ml/min). The results of the analysis are shown in Table 2. The composition of fatty acids turned out to vary greatly between oils, clearly showing that the method of extraction using liquefied dimethyl ether as a solvent had separation selectivity for lipids.

The oils of fraction Nos. 1 and 2 in Table 2 had extremely high values (ca. 80%) for palmitic acid (C16:0) in the composition of fatty acids. The values were higher than that for palmitic acid in the composition of fatty acids as calculated from the sum of the oils in all fractions of Example 1. Therefore, it became clear that the method of extraction using liquefied dimethyl ether as a solvent is capable of fractionation for increasing the proportion of palmitic acid containing lipids which are expected as a biofuel.

What is more, the oils of fraction Nos. 3, 4 and 5 in Table 2 showed higher values for DHA in the composition of fatty acids than that for DHA in the composition of fatty acids as calculated from the sum of the oils in all fractions of Example 1. Therefore, it became clear that the method of extraction using liquefied dimethyl ether as a solvent is capable of fractionation for increasing the proportion of DHA containing lipids.

TABLE 2

| Composition | Fraction No. | | | | | | |
| --- | --- | --- | --- | --- | --- | --- | --- |
| of fatty acids (%) | 1 | 2 | 3 | 4 | 5 | 6 | Total |
| C14:0 | 7.0 | 6.8 | 3.8 | 3.9 | 3.8 | 3.6 | 5.2 |
| C16:0 | 78.0 | 78.8 | 45.1 | 46.6 | 41.4 | 43.7 | 60.1 |
| C18:0 | 2.9 | 2.8 | 1.6 | 1.9 | 2.8 | 4.2 | 2.3 |
| DPA n-6 | 1.4 | 1.5 | 8.9 | 7.8 | 7.1 | 4.8 | 5.2 |
| DHA | 4.7 | 4.1 | 33.8 | 29.2 | 25.4 | 16.3 | 19.0 |
| Others | 6.0 | 6.0 | 6.8 | 10.7 | 19.5 | 27.5 | 8.2 |

Note:
The compositions of fatty acids in the oils with fraction Nos. 1 to 6 are found values and the total compositions of fatty acids are calculated values.

Example 2

Method for Obtaining DHA Concentrated Microbial Oil by Selective Extraction Using Dimethyl Ether The results of Example 1 suggested the possibility for selectively removing C16:0 and like fatty acids from microbial biomass by extraction while allowing the other fatty acids like DHA to remain in the biomass.

The microbial biomass used in Example 1 contained the oil identified in the column of "Feed" in Table 3. When this biomass is subjected to only the extraction of up to fraction No. 2 in Table 2, the resulting biomass will contain, by calculation, a residual oil of the composition indentified in the column of "Biomass after extraction" in Table 3.

From Table 3, it can be seen that by extracting lipids with an increased proportion of palmitic acid containing lipids by the method of extraction using liquefied dimethyl ether as a solvent, it is possible to increase the proportion in the microbial biomass of lipids containing other fatty acids, say, DHA.

The microbial biomass may be used as a feed for further extraction and subjected to extraction with a solvent such as hexane that has low separation selectivity for lipids, whereby lipids with an increased proportion of DHA containing lipids can be extracted with good efficiency.

TABLE 3

|  | Feed | Biomass after extraction |
|---|---|---|
| Oil (mg) | 149 | 105 |
| Composition of fatty acids (%) | | |
| C14:0 | 3.9 | 2.6 |
| C16:0 | 47.8 | 34.3 |
| C18:0 | 1.6 | 1.0 |
| DPA n-6 | 8.8 | 12.0 |
| DHA | 33.9 | 46.8 |
| Others | 4.2 | 3.3 |

Example 3

Extraction of Lipids from *Haematococcus* Alga

Dried biomass of *Haematococcus* alga purchased from Biogenic Co., Ltd. (*Haematococcus pluvialis*, BM070828, yet to be disrupted) was used as microbial biomass and subjected to extraction. To 0.403 g of the microbial biomass, 2.317 g of distilled water was added and the mixture was well stirred to make a sample, which was subjected to extraction using the apparatus of FIG. 1. In the process, the flow rate of liquefied dimethyl ether was set at 10 mL/min. The temperature of the extraction column was set at 20° C. and the pressure at 0.51 MPa. In the process, no operation was conducted for disrupting cells. The amounts of the oils obtained by the same procedures as in Example 1 are shown in Table 4, and the results of subjecting those oils to analysis of the composition of fatty acids are shown in Table 5. The composition of fatty acids turned out to vary greatly between oils, clearly showing that as in Example 1, the method of extraction using liquefied dimethyl ether as a solvent had separation selectivity for lipids.

From the results of Examples 1 and 3, it became clear that the method of fractionating lipids by utilizing the separation selectivity for lipids of liquefied dimethyl ether used as the solvent can be operated independently of the type of microorganisms.

TABLE 4

| | Fraction No. | | | | | | |
|---|---|---|---|---|---|---|---|
| | 1 | 2 | 3 | 4 | 5 | 6 | Total |
| Time (min) | 3.3 | 6.3 | 10.2 | 14.6 | 20.9 | 26.3 | |
| Oil (mg) | 18.2 | 2.6 | 4.4 | 1.8 | 2.4 | 1.6 | 31.0 |

TABLE 5

| Composition | Fraction No. | | | | | |
|---|---|---|---|---|---|---|
| of fatty acids (%) | 1 | 2 | 3 | 4 | 5 | 6 |
| C14:0 | 0.7 | 1.2 | 0.6 | 0.7 | 0.9 | 0.8 |
| C16:0 | 39.4 | 22.0 | 18.0 | 9.2 | 10.9 | 8.5 |
| C18:0 | 2.7 | 6.1 | 4.9 | 4.7 | 6.7 | 4.0 |
| C18:1 n-9 | 15.2 | 10.8 | 9.4 | 4.0 | 4.3 | 3.5 |
| C18:2 n-6 | 9.5 | 9.0 | 8.7 | 3.0 | 2.9 | 2.5 |
| C18:3 n-6 | 1.2 | 4.6 | 4.2 | 3.9 | 5.5 | 7.9 |
| C18:3 n-3 | 2.6 | 2.8 | 2.9 | 1.0 | 1.1 | 0.9 |
| Others | 28.8 | 43.5 | 51.3 | 73.5 | 67.7 | 71.9 |

The weight of astaxanthin in each of the oils obtained in Example 3 was measured by HPLC. An astaxanthin standard compound and the respective oils were dissolved in acetone:chloroform=2:1 for analysis. The conditions for analysis were as follows: column, COSMOSIL 250×4.6 mm (i.d.), 5$C_{18}$-MS-PAQ type (product of Nacalai Tesque, Inc.); detector, Intelligent UV/visible light detector UV-2075 plus (product of JASCO Corporation); mobile phase, methanol:tetrahydrofuran=9:1; flow rate, 1.5 mL/min; detection, 470 nm). The results are shown in Table 6. The colors of the respective oils as seen by visual inspection are also indicated in Table 6. *Haematococcus pluvialis* is a microalga belonging to the class of green algae and contains the lipid soluble pigment chlorophyll (green) as a photosynthetic pigment. It is also known that astaxanthin (red orange) which is another lipid soluble pigment accumulates at high concentration in cyst cells of *Haematococcus pluvialis*. Since the respective oils obtained by extraction using liquefied dimethyl ether as the solvent had distinct color differences, the liquefied dimethyl ether was even verified to have separation selectivity for those lipid soluble pigments. This property of liquefied dimethyl ether may be used to provide a method by which the content of chlorophyll, for example, is reduced, eventually producing an astaxanthin containing oil that presents a brighter, red orange color.

TABLE 6

| | Fraction No. | | | | | |
|---|---|---|---|---|---|---|
| | 1 | 2 | 3 | 4 | 5 | 6 |
| Astaxanthin (μg) | 11.2 | 10.0 | 3.2 | 1.3 | 0.9 | 1.1 |
| Color (to the eye) | green | orange | orange | blackish orange | orange to green | light orange |

INDUSTRIAL APPLICABILITY

In accordance with the present invention, it is possible to extract lipids from microbial biomass containing useful, highly unsaturated fatty acids and at the same time fractionate lipids that are rich in saturated fatty acids and the lipids that are rich in highly unsaturated fatty acids. The present invention provides a method that uses liquefied dimethyl ether not as a mere extraction solvent but as a solvent that performs both extraction and fractionation.

The invention claimed is:

1. A method for fractionating lipids during extraction of the lipids from a microbial biomass, comprising
    extracting lipids from the microbial biomass using liquefied dimethyl ether as a solvent;
    collecting two or more fractions of extracts, wherein the two or more fractions have a fatty acid composition which is different from each other, and wherein the two or more fractions have a different proportion of contents of saturated fatty acids and highly unsaturated fatty acids from each other; and
    removing the liquefied dimethyl ether from each of the two or more fractions.

2. The method according to claim 1, wherein the microbial biomass is biomass obtained by culturing a microorganism in the class Labyrinthulea.

3. The method according to claim 2 wherein the microorganism in the class Labyrinthulea belongs to the genus *Aurantiochytrium*.

4. The method according to claim 1, wherein the microbial biomass is biomass obtained by culturing a microorganism in the class of green algae.

5. The method according to claim 4 wherein the microorganism in the class of green algae belongs to the genus *Haematococcus*.

6. The method according to claim 4, wherein the two or more fractions have a different proportion of contents of chlorophyll and astaxanthin from each other.

7. The method according to claim 1, wherein the extraction from microbial biomass with the liquefied dimethyl ether is performed by using a column.

8. The method according to claim 1, wherein the extraction from microbial biomass with the liquefied dimethyl ether is performed by a batch process.

9. A method for altering composition of lipids in microbial biomass comprising,
   extracting the microbial biomass with liquefied dimethyl ether as a solvent; and
   selectively decreasing the proportion of first lipids in the microbial biomass and concentrating second lipids in the microbial biomass, by making use of the separation selectivity of the liquefied dimethyl ether for lipids of microbial biomass and altering the fatty acid composition in the microbial biomass,
   wherein the first lipids are saturated fatty acids and the second lipids are highly unsaturated fatty acids.

10. A method for producing lipids comprising, extracting the second lipids from the microbial biomass having the altered composition of lipids by the method of claim 9.

11. The method according to claim 10, wherein the microbial biomass is biomass obtained by culturing a microorganism in the class Labyrinthulea.

12. The method according to claim 11 wherein the microorganism in the class Labyrinthulea belongs to the genus *Aurantiochytrium*.

13. The method according to claim 10, wherein the microbial biomass is biomass obtained by culturing a microorganism in the class of green algae.

14. The method according to claim 13 wherein the microorganism in the class of green algae belongs to the genus *Haematococcus*.

15. The method according to claim 9, wherein the microbial biomass is biomass obtained by culturing a microorganism in the class Labyrinthulea.

16. The method according to claim 15 wherein the microorganism in the class Labyrinthulea belongs to the genus *Aurantiochytrium*.

17. The method according to claim 9, wherein the microbial biomass is biomass obtained by culturing a microorganism in the class of green algae.

18. The method according to claim 17 wherein the microorganism in the class of green algae belongs to the genus *Haematococcus*.

* * * * *